United States Patent
Stauss et al.

(10) Patent No.: US 7,197,927 B2
(45) Date of Patent: Apr. 3, 2007

(54) SENSOR FOR DETERMINING THE INTERIOR HUMIDITY AND FOGGING UP TENDENCY AND FASTENING DEVICE OF THE SENSOR

(75) Inventors: Gerold Stauss, Herrenberg (DE); Christoph Raab, Stuttgart (DE)

(73) Assignee: Sitronic Gesellschaft für Elektrotechnische Ausrustüng mbH & Co. KG, Gartringen (DE)

( * ) Notice: Subject to any disclaimer, the term of this patent is extended or adjusted under 35 U.S.C. 154(b) by 10 days.

(21) Appl. No.: 11/050,566

(22) Filed: Feb. 3, 2005

(65) Prior Publication Data

US 2005/0178200 A1    Aug. 18, 2005

(30) Foreign Application Priority Data

Feb. 16, 2004  (DE)  ................ 10 2004 007 341
Oct. 29, 2004   (EP)  ................ 04025714

(51) Int. Cl.
*G01N 1/00* (2006.01)
*G01N 19/10* (2006.01)

(52) U.S. Cl. ................ 73/335.02; 73/29.01; 73/29.05; 374/28; 374/142

(58) Field of Classification Search ................ 73/29.01, 73/335.02, 29.05; 374/28, 142
See application file for complete search history.

(56) References Cited

U.S. PATENT DOCUMENTS

| | | | |
|---|---|---|---|
| 4,984,462 A * | 1/1991 | Hass et al. ................ 73/293 |
| 5,701,752 A | 12/1997 | Tsunokawa et al. |
| 5,753,797 A * | 5/1998 | Forster et al. ............. 73/24.01 |
| 6,422,062 B1 | 7/2002 | King et al. |
| 6,508,408 B2 * | 1/2003 | Kelly et al. ................ 236/91 C |
| 6,668,917 B1 * | 12/2003 | Zeng ............................ 165/202 |
| 6,886,351 B2 * | 5/2005 | Palfy et al. .................... 62/140 |
| 6,978,199 B2 * | 12/2005 | Markow ........................ 701/36 |
| 2001/0032470 A1 | 10/2001 | Remond et al. |
| 2004/0040321 A1 * | 3/2004 | Lo Presti et al. ............. 62/156 |

FOREIGN PATENT DOCUMENTS

| | | |
|---|---|---|
| DE | 197 22 577 A1 | 12/1998 |
| DE | 197 55 008 A1 | 7/1999 |
| JP | 63-180514 A * | 7/1988 ................ 62/243 |

* cited by examiner

*Primary Examiner*—Daniel S. Larkin
(74) *Attorney, Agent, or Firm*—Walter A. Hackler

(57) ABSTRACT

A sensor means is proposed to determine an interior humidity and/or an interior volume delimited by a wall, in particular, of a vehicle passenger compartment 3, and a fogging up tendency of an inner surface of the wall, in particular, of a window 5 of the vehicle passenger compartment 3, with a dew point sensor 10 having a humidity sensor element 1 and a temperature sensor 2, wherein the humidity sensor element 1 and the temperature sensor 2 a thermally coupled, and a surface temperature sensor 4, wherein the dew point sensor 10 is designed to measure the air humidity and the room temperature of the interior volume and the surface temperature sensor 4 is designed to measure the temperature of the inner surface.

11 Claims, 3 Drawing Sheets

SENSOR FOR DETERMINING THE INTERIOR HUMIDITY AND FOGGING UP TENDENCY AND FASTENING DEVICE OF THE SENSOR

This application claims Paris Convention priority of DE 10 2004 007 341.4 filed Feb. 16, 2004, and EP 04 025 714.9 filed Oct. 29, 2004 the complete disclosures of which are hereby incorporated by reference.

BACKGROUND OF THE INVENTION

The present invention concerns a sensor means for determining an interior humidity of an interior volume delimited by a wall, e.g. the passenger compartment of a vehicle, and a fogging up tendency on an inner surface of the wall. The sensor means comprises a dew point sensor with a humidity sensor element and a temperature sensor, wherein the humidity sensor element and the temperature sensor are thermally coupled, and a surface temperature sensor. The sensor arrangement is suitable, in particular, for detecting fogging up on the inner side of a vehicle window and the humidity inside the vehicle.

Several solutions have been suggested to prevent fogging up or to measure the interior humidity. EP 1380481 A2 and EP 1306242 A1 propose mounting of a humidity sensor element directly on the window or in its direct vicinity. This sensor element measures the relative air humidity. The obtained data gives information about the tendency of the window to fog up. EP 1306242 A1 moreover proposes to also consider the temperature in the passenger compartment of a vehicle to prevent fogging up.

WO 02/33395 A1 discloses a dew point sensor. If heat is withdrawn from a gaseous medium, e.g. water vapour, which may happen on the inner surface of a vehicle window, it condenses into liquid, e.g. water, at a certain temperature. This temperature with a certain relative air humidity is called the dew point and can be calculated from a measured relative air humidity (interior humidity) and a measured air temperature. If, at a certain relative air humidity, a surface temperature is close to the dew point, the surface tends to fog up (fogging up tendency), i.e. the liquid condenses on the surface. The dew point sensor has a mounting base on which an air humidity sensor and an air temperature sensor are disposed. The mounting base has a thermally conducting coating which is in thermal contact with the air humidity sensor and the air temperature sensor. Since the air humidity sensor and the air temperature sensor detect data at identical temperatures through thermal contact, the dew point at the location of the mounting base of the dew point sensor can be determined from the detected sensor data.

A disadvantage of the conventional solutions consists in that there is a temperature difference between the humidity sensor and the window surface with the result that the measured relative humidity at the sensor does not correspond to the relative humidity on the window. Exact determination of the fogging up tendency is therefore not possible. Another disadvantage consists in that this arrangement does not provide exact information about the relative air humidity in the passenger compartment, which is a decisive feature of comfort.

It is the underlying purpose of the invention to provide a sensor means and a fastening device for mounting thereof, which eliminate the disadvantages of prior art, wherein, in particular, the fogging up tendency of a support surface, i.e. an inner surface of a wall of an interior volume, in particular, a vehicle window and also the interior humidity of the interior volume, in particular, of a vehicle passenger compartment, are reliably detected.

SUMMARY OF THE INVENTION

The inventive sensor means for determining an interior humidity and/or an interior dew point of an interior volume delimited by a wall, in particular, a vehicle passenger compartment, and a fogging up tendency of an inner surface of the wall comprises a dew point sensor with a humidity sensor element and a temperature sensor, wherein the humidity sensor element and the temperature sensor are thermally coupled, and a surface temperature sensor. Thermal coupling causes the humidity sensor element and the temperature sensor to substantially have the same temperature, i.e. the temperature of the interior, i.e. of the air located therein, or at least a temperature which is directly related to the interior temperature. In accordance with the invention, the dew point sensor is designed to measure the air humidity and room temperature of the interior volume and the surface temperature sensor is designed to measure an inner surface temperature.

In contrast to the prior art, the dew point sensor is intended to be mounted with the humidity sensor element and the temperature sensor in the interior of a vehicle passenger compartment and to mount a further temperature sensor (surface temperature sensor) to a window (pane) of the passenger compartment, whereas the humidity sensor element is conventionally glued to the window. The inventive arrangement permits exact determination of the dew point, since the humidity sensor element and also the temperature probe have the same room temperature and need not be brought to the temperature of the window. Only a sensor, i.e. the surface temperature sensor must be brought to the temperature of the window which requires considerably less effort than bringing two sensors to the temperature of the window. Moreover, the effort of mounting one single temperature probe to the window is considerably less than the effort of mounting two sensors to the window. The assembly costs are thereby larger than the costs of the components of an additional temperature probe. The inventive sensor means permits reliable detection of the fogging up tendency, e.g. of the windscreen. Fogging up of the window can be reliably counteracted e.g. through control by a vehicle air conditioning system. The interior humidity in the vehicle passenger compartment is additionally measured. Both insufficient and excessive air humidity in the passenger compartment both have a negative effect on the well-being of the passengers. If the humidity is measured, the humidity can be controlled to optimum values through air conditioning.

The surface temperature sensor is preferably a contacting temperature sensor, in particular, an NTC or PTC sensor element. This sensor element is mounted to the support surface, in particular the window such that its temperature corresponds to an optimum degree to the temperature of the support surface, in particular the window.

In a preferred manner, a material with good heat conducting properties is introduced between the surface temperature sensor and the support surface, which can compensate for mechanical roughness or tolerances of the support surface or the surface temperature sensor.

The surface temperature sensor is preferably thermally decoupled from the dew point sensor which may be provided, e.g. in that the connection between the sensors, e.g. for coupling to an evaluation unit, is produced from materials having poor heat conducting properties e.g. of plastic material. This decoupling permits measurement of the surface temperature of the inner surface with optimum accuracy using the surface temperature sensor. Moreover, the measurement through the dew point sensor is not falsified through thermal coupling to the inner surface.

The sensor means preferably comprises a printed board, wherein the dew point sensor is mounted to the printed board which facilitates handling of the sensor means during assembly in a vehicle.

In a preferred embodiment of the inventive sensor means, the sensor means has a flexible, thermally conducting sheet which is preferably provided with strip conductors, wherein the surface temperature sensor is mounted to the sheet. The sheet is thereby connected to the printed board, preferably in an electrically conducting manner. This embodiment permits thermal coupling of the surface sensor to the inner surface and connection of the surface temperature sensor to the evaluation unit through use of only one component.

In a further embodiment of the inventive sensor means, the surface temperature sensor is mounted to the printed board. This embodiment is suited, in particular, for quick mounting of the sensor means. In this embodiment of the inventive sensor means, the printed board preferably has an elongated basic shape. The basic shape is formed by a protruding end and a support surface, wherein the surface temperature sensor is mounted to the protruding end and the dew point sensor and the evaluation unit are disposed on the support surface. The elongated basic shape and the described arrangement of the dew point sensor, the evaluation unit and the surface temperature sensor achieve thermal decoupling of the surface temperature sensor from the dew point sensor due to their spatial distance.

In a preferred embodiment, an evaluation unit is preferably provided on the printed board, in particular, on the support surface, which processes the measured signals of the humidity sensor and the temperature sensor located in the direct vicinity of the humidity sensor, and calculates therefrom the dew point.

In a preferred manner, the evaluation unit is designed to correct the measured signal of the surface temperature sensor using a function of the measured signal of the surface temperature sensor and of the temperature sensor on the humidity element through addition or multiplication, and determine therefrom the surface temperature. The surface temperature sensor is not in direct physical contact with the window such that correction of the measured temperature sensor signal might be required. In another preferred manner, the surface temperature determined in this manner is corrected in dependence on signals of a sun sensor, a rain sensor, an external temperature sensor and/or a speed sensor.

The function is preferably added to the measured signal of the surface temperature sensor.

The function is preferably the difference between the measured signals of the surface temperature sensor and the temperature sensor on the humidity element, which is weighted with a constant, thereby obtaining a first approximation for the correction of the measured signal of the surface temperature sensor which is often sufficient for practical applications.

In a particularly advantageous manner, the evaluation unit is designed to compare the calculated dew point with the determined surface temperature and to determine therefrom the fogging up tendency.

The evaluation unit is preferably designed to emit a warning when a relative air humidity value at a mounting point of the surface temperature sensor is exceeded. If the inventive sensor means is used in a vehicle passenger compartment, the mounting point is preferably the inner surface of the windscreen or a point on the printed board, i.e. the point where the surface temperature sensor is mounted. A passenger can thereby prevent fogging up of the windscreen by switching on the vehicle ventilator.

In a particularly preferred manner, the evaluation unit has an interface, in particular, a Kline, CAN or LIN bus, for an air conditioning control, in particular of a vehicle air conditioning control which permits automatic prevention of fogging up of e.g. the windscreen. The evaluation unit can output the dew point of the air in the room, in particular, of the vehicle passenger compartment, and the inner surface temperature of the walls, in particular, the vehicle window. Moreover, the evaluation unit can issue the relative air humidity and temperature on the inner surface of the wall. The evaluation unit can moreover output the relative air humidity and temperature at the position of the humidity sensor.

Reliable air humidity measurement with simultaneous protection of the sensor means from, e.g. dirt, can be realized with the inventive sensor means, in particular, when the sensor means comprises a housing with a lid having a humidity-permeable diaphragm, wherein the dew point sensor is disposed within the housing. The diaphragm ensures that the air humidity at the location of the dew point sensor corresponds to the air humidity in the interior volume.

The sensor means preferably comprises a sensor holder having a front surface, wherein the surface temperature sensor is mounted to the front surface such that the surface temperature sensor can be mounted to the inner surface in a thermally conducting manner, preferably through gluing the front surface to the inner surface. This provides reliable and simple mounting of the surface sensor to an inner surface. Gluing is advantageously effected using an adhesive having good heat conducting properties.

Preferably, a bonding sheet is thereby used which may be covered with a removable protective sheet which additionally facilitates mounting of the surface temperature sensor.

The inventive sensor means is suited, in particular, for installation in a fastening device, wherein the fastening device is designed as rear mirror foot of a rear mirror of a vehicle, and wherein the dew point sensor is mounted within the fastening device. The data for determining the dew point is measured at the location where the rear mirror foot is mounted in the vehicle passenger compartment.

A further embodiment of an inventive fastening device with a sensor arrangement comprises:
  a cover which is designed as a rear mirror foot with installed electronic unit of the sensor arrangement;
  a tubular projection on the cover; and
  a sensor holder which can be pushed onto the projection having a front surface which is adapted to the inner surface of a vehicle window.

The sensor holder is thereby disposed on the projection, such that it can be displaced and that the front surface can rest on the inner surface of the vehicle window through displacing the sensor holder when the rear mirror foot is mounted in the vehicle passenger compartment. This embodiment of a fastening device can be used to mount any sensor arrangement. The inventive sensor means is preferably mounted with the inventive fastening device in the inside of the vehicle. The sensor arrangement comprises an inventive sensor means, wherein the surface temperature sensor is mounted to the front surface such that the surface temperature sensor can be mounted in a thermally conducting manner to the inner surface of the vehicle window, preferably through gluing of the front surface to the inner surface, and the dew point sensor is disposed within the cover. The inventive fastening device provides good protection of the sensor means against dirt and/or damage, in particular, when cleaning the windows. Good thermal connection of the surface temperature sensor to the window is also ensured. The inventive fastening device also ensures simple assembly.

The above described embodiments of the inventive sensor means, wherein the surface temperature sensor is disposed on the printed board, are preferably mounted using a fastening device with a housing which surrounds the sensor means, comprising a holder on a wall of the interior volume. A flexible and heat conducting substance, preferably a silicon heat conducting substance, is thereby disposed on a front surface of the projecting end of the printed board, at a location where the surface temperature sensor is mounted on the printed board. The housing including holder is designed to press the printed board with the substance to an inner surface of the wall, preferably a windscreen. The fastening device of this structure permits fast assembly of the inventive sensor means, wherein the surface temperature sensor is thermally well coupled to the inner surface of the windscreen in an inexpensive manner.

In a preferred embodiment of the fastening device, the flexible heat conducting substance is designed as cap which is pushed onto the end of the printed board at the mounting point of the surface temperature sensor.

In a further preferred embodiment of the fastening device, a metal part, e.g. a stamped-bent part is mounted, e.g. soldered, to the mounting point of the surface temperature sensor. The heat conducting material is disposed on this metal part through injecting or casting around.

Further advantages can be extracted from the description and the enclosed drawing. The features of the invention mentioned above and below may be used individually or in any combination. The embodiments mentioned are not to be understood as exhaustive enumeration but have exemplary character.

The invention is explained in more detail below using embodiments with reference to the drawing. The figures of the drawing show the inventive subject matter in a highly schematized manner and are not to be taken to scale. The individual components of the inventive subject matter are illustrated such that their design is clearly shown.

BRIEF DESCRIPTION OF THE DRAWING

FIG. 3b shows a plan view of the fastening device in accordance with FIG. 3a.

DESCRIPTION OF THE PREFERRED EMBODIMENT

Figure 1:
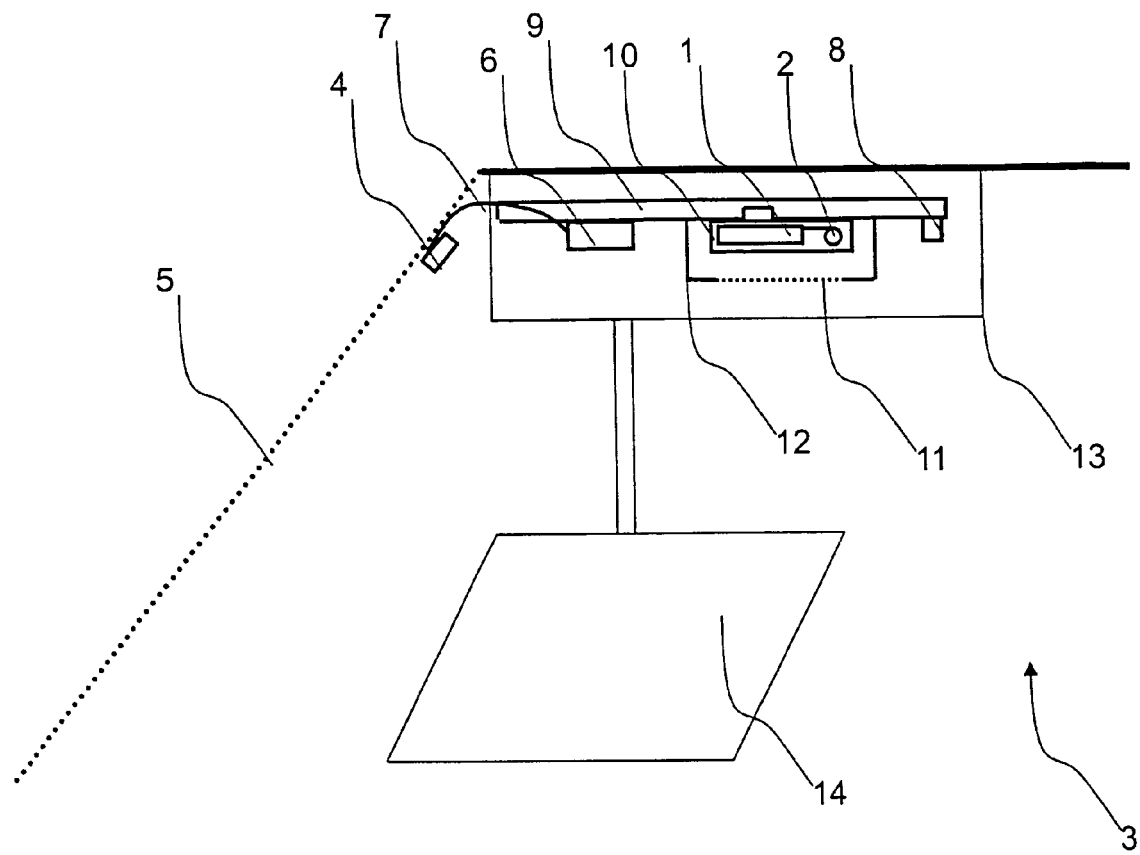
FIG. 1 shows an inventive sensor means which is integrated in a vehicle rear mirror foot which is mounted in a vehicle passenger compartment.

FIG. 1 shows an inventive sensor means which is integrated in a vehicle rear mirror foot 13 which is mounted in a vehicle passenger compartment 3. The inventive sensor means determines the fogging up tendency of the vehicle window 5 through measurement of the relative interior humidity and the interior temperature using the dew point sensor 10. The dew point or the absolute humidity in the interior is determined from this value, as is known from e.g. WO 0233395 A1. The window temperature at one inner surface of the vehicle window 5 is additionally determined using a surface temperature sensor 4. The fogging up tendency of the inner surface is determined from the window temperature and the dew point using the evaluation unit 6. The inventive sensor means for detecting the fogging up tendency and the interior humidity comprises a dew point sensor 10 with a humidity sensor element 1 and a temperature sensor 2 which are thermally well coupled and are disposed in an interior 3, in particular, a vehicle passenger compartment. The inventive sensor means also comprises the surface temperature sensor 4 which determines the surface temperature on the inside of an outer wall of the interior, in particular, the vehicle window 5, and the evaluation unit 6 which evaluates the measured data. The surface temperature sensor 4 is thermally decoupled from the humidity sensor element 1 and the temperature sensor 2. The surface temperature sensor 4 is glued to the inner side of the outer wall, e.g. the vehicle window 5, with an adhesive which has, in particular, good heat conducting properties. The surface temperature sensor 4 is mounted to a flexible sheet 7 which is preferably provided with strip conductors and has good heat conducting properties. The sheet 7 is mounted to the inner side of the wall (outer wall) e.g. to the inner side of the vehicle window 5 thereby ensuring good thermal coupling between the surface temperature sensor 4 and the window 5, since the sheet 7 has good heat conducting properties. Good thermal coupling thereby means that the surface temperature sensor 4 substantially assumes the actual temperature of the inner surface and can calculate therewith. The evaluation unit 6 is connected to an air conditioning control of the interior, e.g. the vehicle passenger compartment 3, via an interface 8. The humidity sensor element 1, the temperature sensor 2 and the evaluation unit 6 are mounted to a printed board 9. The sheet 7 which is provided with the surface temperature sensor 4 is electrically conducting connected to the printed board 9 which is provided with the humidity sensor element 1, the temperature sensor 2 and the evaluation unit 6. The humidity sensor element 1, the temperature sensor 2, the evaluation unit 6 and the surface temperature sensor 4 may all be mounted together on a printed board. In this case, thermal decoupling between the surface temperature sensor 4 and the printed board 9 is required. The arrangement of humidity sensor element 1 and temperature sensor 2, i.e. the dew point sensor 10, is mounted in the foot 13 of a rear mirror 14 of a vehicle. The arrangement of humidity sensor element 1 and the temperature sensor 2 is protected by a housing 12 which comprises a lid with a humidity permeable diaphragm 11. The evaluation unit 6 may be designed to emit a warning, e.g. via the interface 8, when an adjustable threshold of the relative air humidity on the inner surface of the wall, e.g. the vehicle window 5, is exceeded.

Figure 2A:
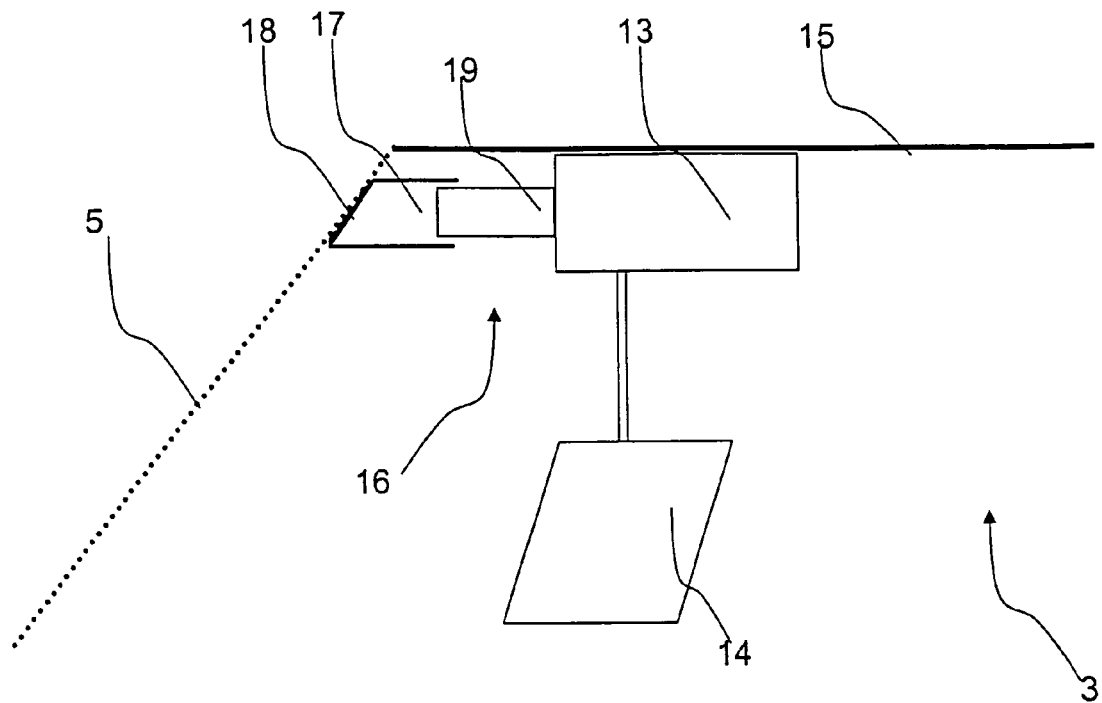
FIG. 2a shows an inventive fastening device designed as vehicle rear mirror foot which is mounted in a vehicle passenger compartment.
Figure 2B:
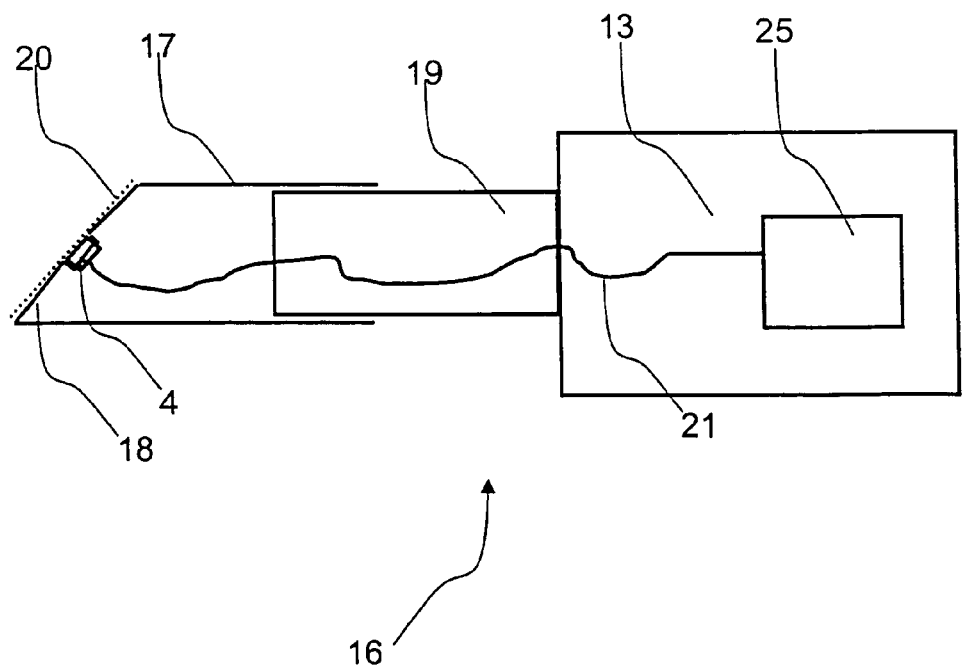
FIG. 2b shows an inventive fastening device with an electronic arrangement installed therein.

FIG. 2a shows an inventive fastening device 16 which is designed as vehicle rear mirror foot 13 which is mounted on the vehicle roof 15 in a vehicle passenger compartment 3. The rear mirror foot 13 forms a cover which is extended by a tubular projection 19. FIG. 2b shows an inventive fastening device 16 with an electronic arrangement 25 which is installed in the cover, e.g. an evaluation unit and/or a dew point sensor of an inventive sensor means and/or further sensors, preferably however, consisting of humidity sensor, temperature sensor and evaluation unit. The electronic unit 25 is installed on the cover, i.e. in the rear mirror foot 13 and is connected to the surface temperature sensor 4 using an electric feed line 21. A sensor holder 17 is pushed onto the projection 19. Before mounting the mirror foot 13 in the vehicle, the sensor holder 17 is completely pushed to the cover or the mirror foot 13, wherein sliding off is prevented through suitable constructive measures, e.g. a locking groove. The front surface 18 of the sensor holder 17 is designed to be adapted to the windscreen 5. The surface temperature sensor 4 is moreover integrated in the front surface 18 of the sensor holder 17 such that the surface temperature sensor 4 finishes level with the front surface 18, i.e. there is a tight contact between the surface temperature sensor 4 and the windscreen 5 in the assembled state. A bonding sheet 20 or the like is provided on the front surface 18 for mounting the sensor holder 17 to the windscreen 5. The front surface 18 forms a contact surface with a bonding sheet 20 can be recessed at the location of the surface temperature sensor 4. The front surface 18 and the bonding sheet 20 are provided with a protective sheet before installation.

To install the rear mirror 14, initially the protective sheet is removed and subsequently the rear mirror foot 13 or the cover is mounted or vice versa. Subsequently, the sensor holder 17 is pushed to the windscreen 5 and glued.

Figure 3A:
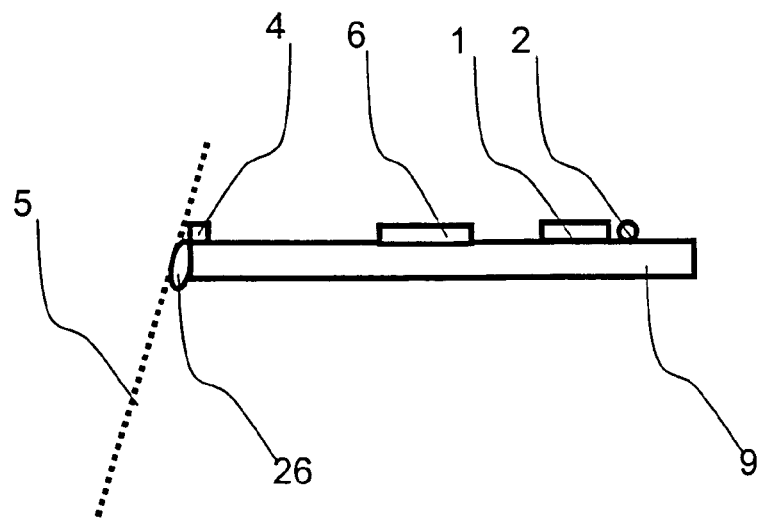
FIG. 3a shows a side view of a further inventive fastening device.
Figure 3B:
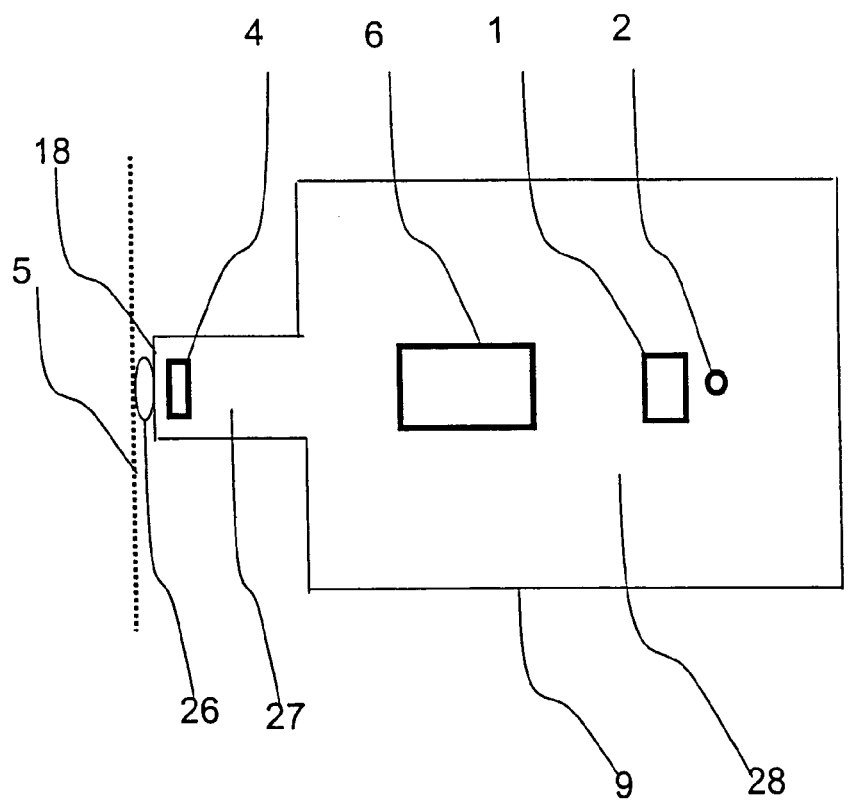

FIG. 3a shows a side view of a further embodiment of an inventive fastening device and FIG. 3b shows a top view thereof. This embodiment of an inventive fastening device with a sensor arrangement comprises:

- a printed board 9 with mounted humidity sensor element 1, temperature sensor 2, evaluation unit 6 and surface temperature sensor 4 as components. The printed board 9 has an elongated basic shape. This basic shape consists of a projecting end 27 and a support surface 28. The arrangement of the components on the printed board 9 is selected such that the surface temperature sensor 4 is thermally decoupled from the rest of the components on the printed board 9. Towards this end, the surface temperature sensor 4 is mounted to the projecting end 27 of the printed board 9 and the remaining components are disposed on the support surface 28.
- a flexible heat conducting substance 26, e.g. heat conducting silicon adhesive, is disposed on a front surface 18 of the projecting end 27 of the printed board 9 at the mounting point of the surface temperature sensor 4. The substance 26 provides tight, heat conducting contact with the windscreen 5 and compensates for mechanical tolerances due to its flexibility.
- a housing with holder (which is not shown in the figures) which forces the printed board 9 including substance 26 to the windscreen 5.

The invention is not limited to the above-mentioned embodiments. Various variants are feasible which also utilize the features of the invention in basically different embodiments.

List of Reference Numerals
1 humidity sensor element
2 temperature sensor
3 vehicle passenger compartment
4 surface temperature sensor
5 window
6 evaluation unit
7 sheet
8 interface
9 printed board
10 dew point sensor
11 diaphragm
12 housing
13 vehicle rear mirror foot
14 vehicle rear mirror
15 vehicle roof
16 fastening device
17 sensor holder
18 front surface
19 projection
20 bonding sheet
21 electric feed line
25 electronic unit
26 heat conducting silicon mass
27 projecting end
28 support surface

We claim:

1. Sensor for determining an interior humidity or an interior dew point of an interior volume delimited by a wall, and a fogging up tendency of an inner surface of the wall, said sensor comprising:
   a printed board;
   a dew point sensor, mounted to the printed board, having a humidity sensor element measuring air humidity of the interior volume;
   a temperature sensor, mounted to the printed board, measuring room temperature of the interior volume; and
   a surface temperature sensor measuring a temperature of the inner surface, said printed board having an elongated basis shape consisting of a protruding end and a support surface, the surface temperature sensor is mounted to the protruding end and the dew point sensor is disposed on the support surface.

2. Sensor according to claim 1, wherein the surface temperature sensor is a contacting sensor, including an NTC or PTC sensor element.

3. Sensor according to claim 2, further comprising a material having good heat conducting properties disposed between the surface temperature sensor and the wall.

4. Sensor according to claim 2, wherein the surface temperature sensor is thermally decoupled from the dew point sensor.

5. Sensor according to claim 1, further comprising an evaluation unit disposed on the printed board, in particular on the support surface, and is designed to calculate the dew point from the measured signal of the dew point sensor.

6. Sensor according to claim 5, wherein the evaluation unit comprises a Kline, CAN, or LIN bus interface with a vehicle air conditioning control system.

7. Sensor according to claim 1, wherein the sensor comprises a housing having a lid with a humidity permeable diaphragm, and wherein the dew point sensor is disposed within the housing.

8. Sensor according to claim 1, wherein the sensor comprises a sensor holder with a front surface, and wherein the surface temperature sensor is mounted to the front surface such that the surface temperature sensor can be mounted in a thermally conducting manner to the inner surface, through gluing of the front surface to the inner surface.

9. Sensor according to claim 8, wherein the front surface comprises a bonding sheet comprising a removable protective sheet.

10. Fastening device with a sensor arrangement, comprising: a cover designed as a rear mirror foot, into which an electronic unit of the sensor arrangement is installed; a tubular projection and a sensor holder which can be pushed onto the projection with a front surface which is adapted to an inner surface of a vehicle window; and wherein the sensor holder is displaceably disposed on the projection and the front surface is adapted for connection to the vehicle window through displacing the sensor holder when the rear mirror foot is mounted in a vehicle passenger compartment.

11. Fastening device according to claim 10, wherein the sensor arrangement comprises a sensor for determining an interior humidity or an interior dew point of an interior volume of the vehicle passenger compartment, and a fogging up tendency of a window of the vehicle passenger compartment, said sensor comprising:

- a dew point sensor having a humidity sensor element, measuring air humidity of the interior volume, a temperature sensor measuring room temperature of the interior volume and;
- a surface temperature sensor measuring a temperature of the inner surface,
- wherein the surface temperature sensor is mounted to the front surface such that the surface temperature sensor can be mounted in a thermally conducting manner to the inner surface of the vehicle window through gluing the front surface to the inner surface, and the dew point sensor is disposed within the housing.

* * * * *